United States Patent
Lee

(10) Patent No.: US 11,416,360 B2
(45) Date of Patent: Aug. 16, 2022

(54) SYSTEMS AND METHODS FOR DETECTING ERRORS IN ARTIFICIAL INTELLIGENCE ENGINES

(71) Applicant: FUJIFILM MEDICAL SYSTEMS U.S.A., INC., Morrisville, NC (US)

(72) Inventor: Marianne Lee, Plano, TX (US)

(73) Assignee: FUJIFILM MEDICAL SYSTEMS U.S.A., INC., Morrisville, NC (US)

( * ) Notice: Subject to any disclaimer, the term of this patent is extended or adjusted under 35 U.S.C. 154(b) by 499 days.

(21) Appl. No.: 16/597,457

(22) Filed: Oct. 9, 2019

(65) Prior Publication Data

US 2021/0109829 A1    Apr. 15, 2021

(51) Int. Cl.
*G06F 11/22* (2006.01)
*G16H 30/20* (2018.01)
*G16H 50/20* (2018.01)
*G06N 5/04* (2006.01)
*G06T 7/00* (2017.01)

(52) U.S. Cl.
CPC .......... *G06F 11/2257* (2013.01); *G06N 5/04* (2013.01); *G06T 7/0012* (2013.01); *G16H 30/20* (2018.01); *G16H 50/20* (2018.01)

(58) Field of Classification Search
CPC .... G06F 11/2257; G16H 30/20; G16H 50/20; G06N 5/04; G06T 7/0012
USPC ......................................................... 714/26
See application file for complete search history.

(56) References Cited

U.S. PATENT DOCUMENTS

| | | | | |
|---|---|---|---|---|
| 8,923,580 | B2* | 12/2014 | Dekel | G16H 30/40 382/128 |
| 2013/0129165 | A1* | 5/2013 | Dekel | G16H 30/20 382/128 |
| 2014/0096077 | A1* | 4/2014 | Jacob | G06F 3/013 715/810 |
| 2014/0145935 | A1* | 5/2014 | Sztuk | G06T 7/74 345/156 |
| 2015/0331995 | A1* | 11/2015 | Zhao | G16H 10/60 705/2 |
| 2016/0317046 | A1* | 11/2016 | Fonte | G06N 7/005 |
| 2018/0101645 | A1* | 4/2018 | Sorenson | G06V 30/194 |
| 2018/0137244 | A1* | 5/2018 | Sorenson | G16H 30/40 |
| 2018/0144243 | A1* | 5/2018 | Hsieh | G06F 30/20 |
| 2018/0373620 | A1* | 12/2018 | Thomson | G06F 11/3696 |
| 2019/0052701 | A1* | 2/2019 | Rathod | H04L 51/046 |
| 2019/0180862 | A1* | 6/2019 | Wisser | G16H 30/40 |
| 2019/0214138 | A1* | 7/2019 | Aoyagi | G16H 50/70 |
| 2019/0307335 | A1* | 10/2019 | Bruce | A61B 5/02055 |
| 2020/0082943 | A1* | 3/2020 | Sakaguchi | G06N 3/08 |

(Continued)

FOREIGN PATENT DOCUMENTS

WO    WO 2018/104834 A1    6/2018

*Primary Examiner* — Tauqir Hussain
(74) *Attorney, Agent, or Firm* — Baker Botts L.L.P.

(57) ABSTRACT

A system, method, and apparatus for detecting errors in an artificial intelligence engine. The method includes processing a medical image of a patient at an artificial intelligence engine, and producing a first test result at the artificial intelligence engine based on the medical image. The method also includes detecting an error in the first test result using a server emulator, and producing a second test result that corrects the error in the first test result. In addition, the method includes transmitting the second test result from the artificial intelligence engine to a picture archiving and communication systems server.

20 Claims, 5 Drawing Sheets

(56) References Cited

U.S. PATENT DOCUMENTS

| | | | |
|---|---|---|---|
| 2020/0090229 A1* | 3/2020 | Smith Pask | G06Q 30/0242 |
| 2020/0211692 A1* | 7/2020 | Kalafut | G06N 20/00 |
| 2021/0109829 A1* | 4/2021 | Lee | G16H 40/67 |
| 2022/0043059 A1* | 2/2022 | Cruz | G01R 31/31707 |

* cited by examiner

SYSTEMS AND METHODS FOR DETECTING ERRORS IN ARTIFICIAL INTELLIGENCE ENGINES

BACKGROUND

1. Field of Disclosed Subject Matter

The disclosed subject matter is directed to systems and methods for performing error detection when rendering digital records, for example, medical image records, and more specifically Digital Imaging and Communications in Medicine ("DICOM") objects. The medical image records can be processed by an artificial intelligence engine, and the resulting output can be transmitted to a DICOM server or to a user's workstation.

2. Description of Related Art

In medical imaging, Picture Archiving and Communication Systems ("PACS") are a combination of computers and networks dedicated to the storage, retrieval, presentation, and distribution of images. While images may be stored in a variety of formats, a common format for image storage is DICOM. DICOM is a standard in which, among other things, medical images and associated meta-data can be communicated from imaging modalities ("e.g., X-ray, computed tomography ("CT"), and magnetic resonance imaging ("MRI") apparatuses") to the PACS for storage and from PACS to a client device for viewing by a user, such as medical personnel.

There has been an increased emphasis in recent years on the use of artificial intelligence ("AI") in various applications. In particular, AI engines can be used to help process medical information, and output a potential medical diagnosis based on the processed information. But AI also has potential application in connection with medical imaging. Accordingly, there is a need for a system and method to help facilitate and improve communications between AI engines and the PACS.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to performing error detection when rendering digital records, for example, medical image records, and more specifically DICOM objects. For example, a method can include processing a medical image of a patient at an artificial intelligence engine. The method can also include producing a first test result at the artificial intelligence engine based on the medical image, and detecting an error in the first test result using a server emulator. The medical image can be a DICOM object. In addition, the method can include producing a second test result that corrects the error in the first test result. The method can further include transmitting the second test result from the artificial intelligence engine to a picture archiving and communication systems server. The second test result can include an indication that the detected error was fixed.

In certain non-limiting embodiments, the first test result and the second test result can include a diagnosis made by the artificial intelligence engine based on the medical image. The detecting of the error can also include comparing the first test result to a template javascript object notation, and determining that the first test result does not match a header field or formatting character included in the template javascript object notation. The method can also include validating that the produced second test result does not comprise the error included in the first test result, and that the produced second test result does not include any other error In certain non-limiting embodiments, the method can include creating an error log that comprises the detected errors of the first test result, and inserting the error log into the transmitted second test results. The error log can identify an application programming interface of the server emulator that exhibits the error.

In certain non-limiting embodiments, the method can include receiving a scan notification at the artificial intelligence engine. The method can also include transmitting a token request to the server in response to the scan notification. The request can include a username and password for accessing the token.

In certain non-limiting embodiments, an artificial intelligence engine can include at least one memory comprising computer program code, and at least one processor. The computer program code can be configured, when executed by the at least one processor, to cause the artificial engine to process a medical image of a patient, and produce a first test result based on the medical image. The computer program code can also be configured, when executed by the at least one processor, to cause the artificial engine to detect an error in the first test result using a server emulator. In addition, the computer program code can be configured, when executed by the at least one processor, to cause the artificial engine to produce a second test result that corrects the error in the first test result, and transmit the second test result to a picture archiving and communication systems server.

As further disclosed herein one or more computer-readable non-transitory storage media embodying software are provided. The software can be operable when executed to process a medical image of a patient at an artificial intelligence engine, and produce a first test result at the artificial intelligence engine based on the medical image. The software can also be operable when executed to detect an error in the first test result using a server emulator, and produce a second test result that corrects the error in the first test result. In addition, the software can be operable when executed to transmit the second test result from the artificial intelligence engine to a picture archiving and communication systems server.

DRAWINGS

DETAILED DESCRIPTION

Reference will now be made in detail to the various exemplary embodiments of the disclosed subject matter, exemplary embodiments of which are illustrated in the accompanying drawings. The methods and systems described herein can be used for facilitating communication between an AI engine and the PACS. For example, certain embodiments can help to determine any errors included in the results outputted by the AI engine. The errors can be corrected before the AI engine outputs results to the PACS, thereby helping to prevent erroneous or faulty results from being transmitted to the PACS. Certain embodiments disclosed herein can therefore help to improve the performance of the AI engine, while also decreasing of amount of network resources dedicated by the PACS for dealing with erroneous results received from the AI engine.

A variety of records are suitable for retrieval by the present disclosure and the records can be stored in any system, for example a PACS or Vendor Neutral Archive ("VNA"). For purpose of illustration and not limitation, the systems and methods are described herein with respect to transferring medical image records ("referred to hereinafter as "medical image records" or "records""), specifically DICOM records, stored on a PACS system using DICOM messaging services and DICOM web services, however the methods and system herein can be used for transferring digital records using any transfer protocols. As used in the description and the appended claims, the singular forms, such as "a," "an," "the," and singular nouns, are intended to include the plural forms as well, unless the context clearly indicates otherwise. Accordingly, as used herein, the term medical image record can refer to one medical image record or a plurality of medical image records. For example, and with reference to FIG. 1 for purpose of illustration and not limitation, as referred to herein a medical image record can include a single DICOM Service-Object Pair ("SOP") Instance ("also referred to as "DICOM Instance" "DICOM image" and "image""), one or more DICOM SOP Instances can be included in one or more series, and one or more series can be included inside one or more studies.

Figure 1:
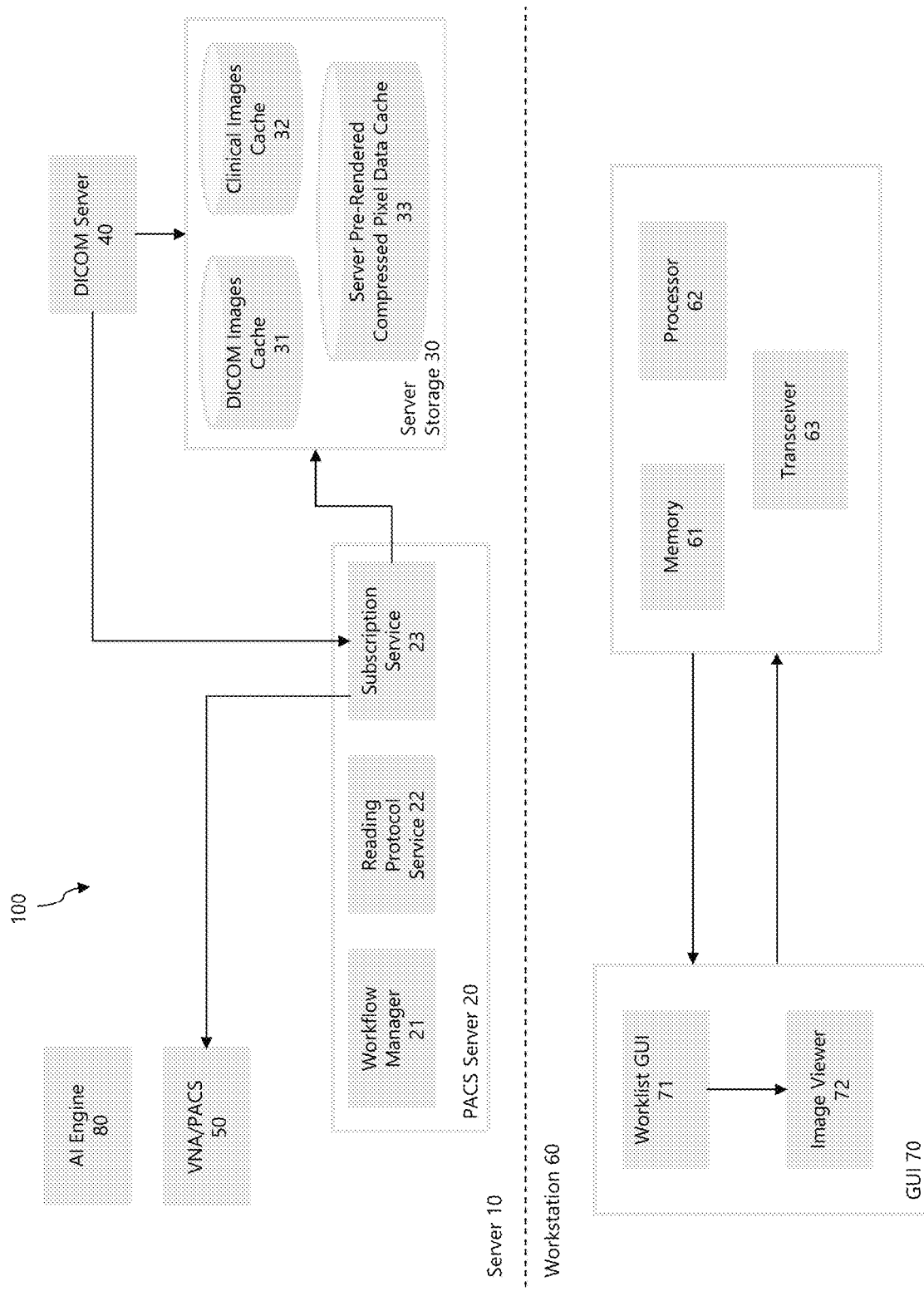
FIG. 1 illustrates an architecture of a system for transferring and rendering medical image records according to certain embodiments of the disclosed subject matter.

FIG. 1 illustrates the architecture of a system for transferring and rendering medical image records according to certain embodiments of the disclosed subject matter. In particular, FIG. 1 illustrates system 100 that can include one or more computing devices defining a server side 10 and a user workstation 60 coupled to the one or more computing devices by a network. The computing device, for example can be a server or client device, while the network, for example, can be a Local Area Network ("LAN"), a Wireless LAN ("WLAN"), a virtual private network ("VPN"), or any other network that allows for any radio frequency or wireless type connection. For example, other radio frequency or wireless connections can include, but are not limited to, one or more network access technologies, such as Global System for Mobile communication ("GSM"), Universal Mobile Telecommunications System ("UMTS"), General Packet Radio Services ("GPRS"), Enhanced Data GSM Environment ("EDGE"), Third Generation Partnership Project ("3GPP") Technology, including Long Term Evolution ("LTE"), LTE-Advanced, 3G technology, Internet of Things ("IOT"), fifth generation ("5G"), or new radio ("NR") technology. Other examples can include Wideband Code Division Multiple Access ("WCDMA"), Bluetooth, IEEE 802.11b/g/n, or any other 802.11 protocol, or any other wired or wireless connection.

As shown in FIG. 1, an AI engine 80 can be included within server 10. AI engine 80 can include hardware and/or software allowing it to communicate with any hardware included in server 10 or in workstation 60 over any known network. In some embodiments, AI engine 80 can be cloud-based. While AI engine 80 is shown as being included in server side 10 in FIG. 1, in other embodiments AI engine 80 can be a separate server or processor operating outside server 10. In some examples, AI engine 80 can be any known AI engine, such as TensorFlow, Keras, Microsoft Azure, Google Cloud Prediction API, or any other AI engine. An AI engine 80 located outside server 10 can be referred to as a third-party server, for example. Even if AI engine 80 is termed a third-party server, however, AI engine 80 can still communicate with either PACS server 10 or workstation 60 using any possible wired or wireless connection or network.

System 100 can be configured to ensure one or more medical images or medical image records are transferred from server 10 to workstation 60. The one or more medical images or records can be cached in workstation 60 before a user opens the images or records at workstation.

A user can be any person authorized to access workstation 60, including any health professional, medical technician, or a patient. In some embodiments a user authorized to communicate with the PACS can have a username and/or password that can be used to login or access workstation 60. System 100 can help to provide an improved reading experience in all network environments, including when workstation 60 is accessed on-premises or remotely.

In certain non-limiting embodiments, server 10 can include a PACS server module 20, a server storage 30, a DICOM server 40, and/or an additional data source, such as a VNA/PACS 50, remote PACS, VNA, or another vendor PACS/VNA. Workstation 60 can include a Graphical User Interface ("GUI") 70, memory or storage 61, processor 62, and/or transceiver 63. A user working at workstation 60 can subscribe to a worklist using worklist GUI 71 of the GUI 70. The user can view the images and/or records on image viewer 72. Image viewer 72 can include any hardware and/or software used to display an images or records. In certain embodiments, image viewer 72 can include a touch screen that allows a user to input information to workstation 60 directly though image viewer 72.

Workstation 60 can receive one or more images or records from server 10 using transceiver 63. Transceiver 63 can, independently, be a transmitter, a receiver, or both a transmitter and a receiver, or a unit or device that can be configured both for transmission and reception. In other words, transceiver 63 can include any hardware or software that allow workstation 60 to communicate with server 10 and/or AI engine 80. Transceiver 63 can be either a wired or a wireless transceiver. When wireless, the transceiver, in certain embodiments, can be implemented as a remote radio head which is not located in the device itself, but in a mast. While FIG. 1 only illustrates a single transceiver, workstation 60 can include one or more transceivers.

All of the images received by workstation 60 can be processed using one or more processors 62. Processor 62 can be any hardware or software used to execute computer program instructions. These computer program instructions can be provided to a processor of a general purpose computer to alter its function to a special purpose, a special purpose computer, application-specific integrated circuit ("ASIC"), or other programmable digital data processing apparatus, such that the instructions, which execute via the processor of the client station or other programmable data processing apparatus, implement the functions/acts specified in the block diagrams or operational block or blocks, thereby transforming their functionality in accordance with embodiments herein. In certain non-limiting embodiments, the processor can be a portable embedded micro-controller or micro-computer. For example, processor 62 can be embodied by any computational or data processing device, such as a central processing unit ("CPU"), digital signal processor ("DSP"), application specific integrated circuit ("ASIC"), programmable logic devices ("PLDs"), field programmable gate arrays ("FPGAs"), digitally enhanced circuits, or comparable device or a combination thereof. The processors can be implemented as a single controller, or a plurality of controllers or processors.

In certain embodiments, the records and/or images received at workstation 60 can be cached in memory 61 of workstation 60. Memory 61 can be a non-volatile storage medium or any other suitable storage device, such as a non-transitory computer-readable medium or storage medium. For example, memory 61 can be a random-access memory ("RAM"), read-only memory ("ROM"), hard disk drive ("HDD"), erasable programmable read-only memory ("EPROM"), electrically erasable programmable read-only memory ("EEPROM"), flash memory or other solid-state memory technology. Memory 61 can also be a compact disc read-only optical memory ("CD-ROM"), digital versatile disc ("DVD"), any other optical storage, magnetic cassettes, magnetic tape, magnetic disk storage or other magnetic storage devices, or any other physical or material medium which can be used to tangibly store the desired information or data or instructions and which can be accessed by a computer or processor. Memory 61 can be either removable or non-removable.

Workstation 60 can take the form of any known client device. For example, workstation 60 can be a computer, such as a laptop or desktop computer, a personal data or digital assistant ("PDA"), or any other user equipment or tablet, such as a mobile device or mobile portable media player. Server 10, on the other hand, can be a service point which provides processing, database, and communication facilities. For example, the server can include dedicated rack-mounted servers, desktop computers, laptop computers, set top boxes, integrated devices combining various features, such as two or more features of the foregoing devices, or the like. Servers can vary widely in configuration or capabilities, but can include one or more processors, memory, and/or transceivers. A server can also include one or more mass storage devices, one or more power supplies, one or more wired or wireless network interfaces, one or more input/output interfaces, and/or one or more operating systems.

Although FIG. 1 illustrates memory 61, processor 62, and/or transceiver 63 as being included in workstation 60, server 10 and AI engine 80 can similarly include a memory, a processor, and/or a transceiver. For example, server storage 30 shown in FIG. 1 can correspond to memory 61, while DICOM server 40 can correspond to processor 62.

In some embodiments, server 10 can include a PACS server 20 with workflow manager 21, reading protocol service 22, and/or subscription service 23. Workflow manager 21, for example, can receive requests for records and/or images from workstation 60. Based on the user's subscription, subscription service 23 can coordinate with VNA/PACS 50, DICOM server 40, and server storage 30 to obtain the requested images and/or records. Reading protocol service 22 in PACS server 20 can also be used to identify prior records and/or images that have been stored by server 10. Protocol service 22, for example, can have access to a patient's history and can filter out non-relevant prior images or records based on the preference of the user.

The status of the images and/or records cached in workstation 60 can be displayed in the worklist GUI 71. The user can have the option to remove any record or image from the cache. For example, the cache can be cleared based on rules set by user preference. The cache can be cleared using one or more of the following rules: (1) manually cleared by the user; (2) cleared upon the user logging off the workstation 60; (3) cleared upon the user closing the worklist 5; (4) cleared based on a time limit for storage; (5) cleared based on maximum number of images, instances, series, or studies kept in the cache; or other similar rules.

Caching the images and/or records can include downloading one or more DICOM images and storing the downloaded images in memory 61 of workstation 60. Subscription service 23 can be used to identify the applicable DICOM images stored in server storage 30. Server storage 30 can include DICOM images cache 31, clinical images cache 32, and/or server pre-rendered and compressed pixel data cache 33. In certain embodiments one or more images or records can be stored in an external storage, such as VNA/PACS 50. In such embodiments, subscription service 23 can query the VNA/PACS 50 to obtain a list of DICOM images or records. The queries can be made using a DICOM messaging protocol, a Web Access for DICOM Objects ("WADO") operation ("such as or WADO-RS"), or HyperText Transfer Protocol ("HTTP").

When workstation 60 receives an image from server 10, the image can be rendered in any possible data form. For example, the image can be rendered as a Portable Network Graphics ("PNG") file, used for higher quality viewing, as a Joint Photographic Experts Group ("JPEG") file, used for lower quality viewing, as a Moving Picture Experts Group ("MPEG") file, or any other image file format. In certain embodiments, the images may be stored, received, and/or transmitted at workstation 60 or server 10 in a compressed format. Compressed images, for example, can be cached in server 33 included in server storage 30. Once received, workstation 60 can decompress and display the image in GUI 70.

In certain non-limiting embodiments, system 100 can transmit and receive any communication using HTTP. In certain other embodiments, however, any other protocol can be used, such as Hypertext Transfer Protocol Secure ("HTTPS"). HTTP communications are based on messages ("requests or responses") exchanged between a client and a server. For example, the client can be an AI engine 80 shown in FIG. 1 or 80 shown in FIG. 2, while the server can be emulating server 220 shown in FIG. 2.

In certain embodiments, an HTTP request can include a request line and a header field, followed by an optional message body. The request line can include a one-term command, often referred to as a method, that specifies the nature of the HTTP request message. For example, the request line can include at least one of a GET, POST, HEAD, OPTIONS, PUT, DELETE, TRACE, and/or CONNECT used to determine the nature of the request. The GET request can be used to request data from a specified resource, while a POST request can be used to send data to a server in order to create and/or update a given resource. The HEAD request, on the other hand, can be similar to the GET request, although the HEAD request can exclude a response body. The PUT request can be similar to the POST request, except that the PUT request can be idempotent. The DELETE request can be a request to deliver a specific resource, while the OPTION request merely describes communication options for a specific resource. The TRACE request can be a message loop-back test that is performed along a path to the specific resource. The CONNECT request can establish a tunnel to the server identified by a given Uniform Resource Identifier ("URI"). Other than the above one-term commands or methods, the request line can also include a path component of a Uniform Resource Locator ("URL") for the request, and/or an HTTP version number.

In addition to the request line, an HTTP request can include an HTTP header or header field. The header field, for example, can provide additional information about the message and/or the sender. In other words, the header field can include information that a server can use to determine how to respond to a request. The header field, for example, can include a field name and value. An optional body message can also be included in the HTTP request. An empty line can be placed between the optional body message and the header field to signify the end of the header field. The optional body message can include any additional text the sender would like the recipient to know.

After an HTTP request is received, a server can transmit an HTTP response to a client. The response can provide the client with the requested resource, and/or inform the client that the action has been carried out or that an error has occurred. In certain embodiments the HTTP response can include a status line, an HTTP header or header field, and/or a message body. The status line, for example, can include a status code that indicates the results of the request and/or a reason phrase. The reason phrase can be a textual description of the status code. The header field in the response can be similar to the header field of the HTTP request. The header field can also include information about the response or server, such as a time stamp when the response was transmitted, and/or a format of an image included in the response. An empty line or space can be placed between the header field and the message body. The message body can include the specific resource or information requested by the client.

In certain non-limiting embodiments, an AI engine 80 can be integrated into PACS to help with analysis and/or diagnosis based on DICOM objects. To improve communication between AI engine 80 and PACS, it can be helpful to provide a mechanism for detecting any errors in the test result outputted by AI engine 80. Errors, for example, can include missing one or more header fields and/or being outputted in a wrong or undesirable format. In another example, an error can be a wrong authorization or authentication token included in the test result, or even failing to include an authorization or authentication token all together. To help detect errors in the outputted results of AI engine 80, certain embodiments can process the test results using an emulating server 220, as shown in FIG. 2.

Figure 2:
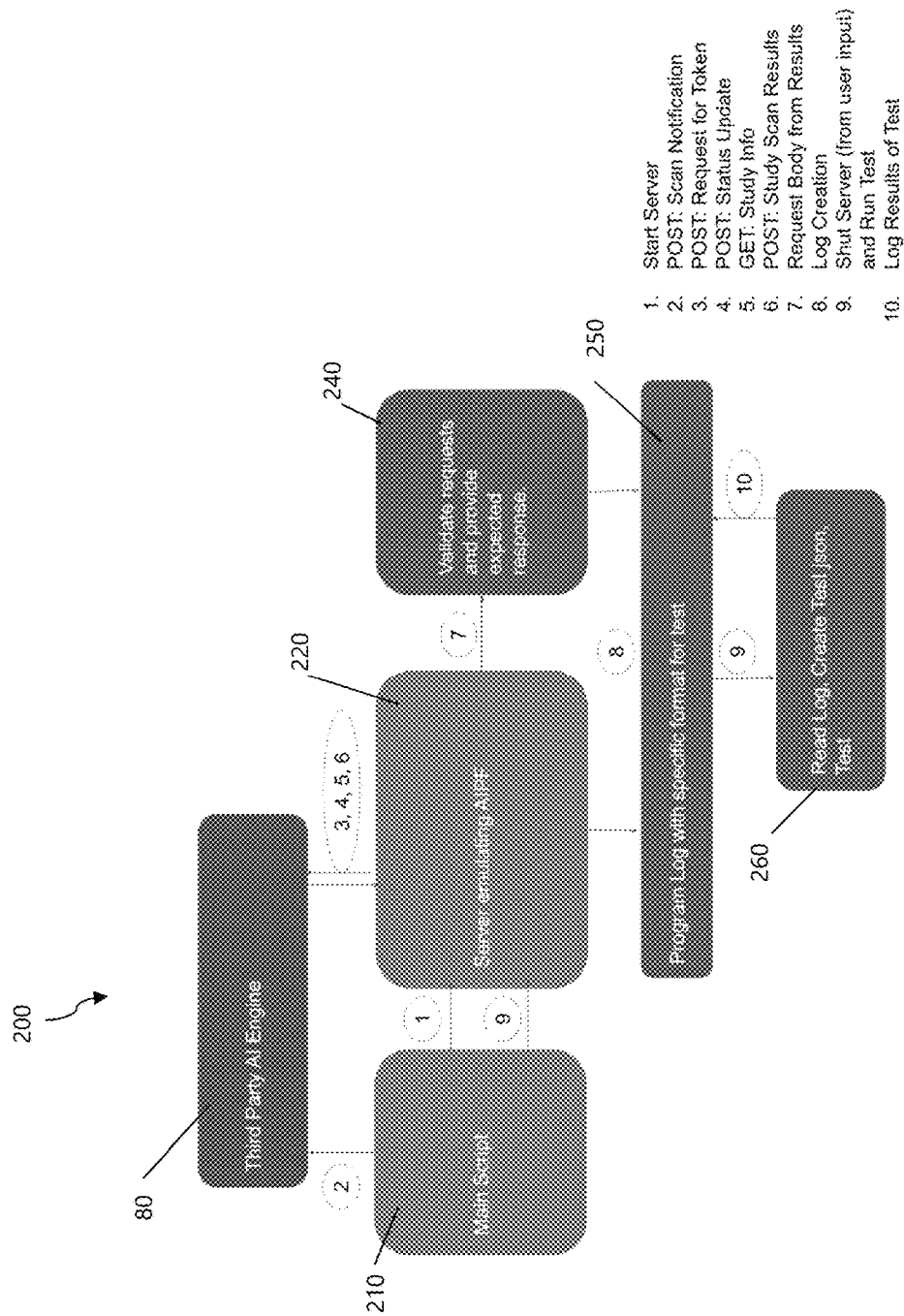
FIG. 2 illustrates a system flow diagram according to certain embodiments of the disclosed subject matter.

FIG. 2 illustrates a system flow diagram according to certain embodiments of the disclosed subject matter. In particular, FIG. 2 illustrates a system 200 for detecting errors in test results produced or outputted by an AI engine 80 using a server emulator 220, also referred to as an emulation server or an emulating server. In certain non-limiting embodiments main script 210 can use a configuration file to start or turn on emulation server 220. Main script 210, for example, can be embodied as software or a computer code program that can operate on the AI engine 80. Although AI engine 80 in FIG. 2 is described as a third-party AI engine, AI engine 80 can alternatively be included within the PACS server, such as server 10 shown in FIG. 1, or be a separate AI engine 80 that can communicate with the PACS server.

In certain non-limiting embodiments, emulation server 220 can run on a virtual machine. In other embodiments emulation server 220 can be embodied as any software and/or hardware component.

AI engine 80 can receive a scan notification from main script 210. The scan notification can take the form of a POST request. In response to the scan notification, AI engine 80 can transmit a token request to server emulator 220. The token request can take the form of a POST request. The request, for example, can include a username and password for authenticating AI engine 80. If the username and password match the user information included in the database of the emulation server 220, the token can be transmitted to AI engine 80. In certain non-limiting embodiments, the token can be included in the test result outputted by AI engine 80.

After a finite amount of time a status update can be transmitted from AI engine 80 to emulation server 220. In certain embodiments the status update can be transmitted as soon as the scan notification is transmitted to AI engine 80, while in other embodiments the status update can be transmitted after AI engine 80 processes the images from the GET request. The status update, which can be in the form of a POST request, can inform emulation server 220 that AI engine 80 does not have a current scan cached or queued. In other words, the transmitted status update can indicate that AI engine 80 is active, meaning that its available to receive and scan medical images. After the status update is transmitted, a GET request for one or more medical images can be transmitted from AI engine 80 to server emulator 220. The one or more medical images can be referred to as study information in FIG. 2. On the other hand, in certain embodiments in which AI engine 80 is actively scanning or processing one or more cached or queued medical images, AI engine 80 can transmit a queued status notice to server emulator 220.

Once AI engine 80 processes the one or more medical images it can output a first test result, also referred to as a study scan result. The first test result can include a medical diagnosis or recommendation made by AI engine 80 based on the processed medical image, and can be transmitted as a POST request to emulation server 220. Specifically, the test result or diagnosis can be included in the body of the POST request. Emulation server 220 can then proceed to validate the request and provide the expected response, as shown in process 240 in FIG. 2. In other words, process 240 can be used to debug the test result outputted by AI engine 80, with the errors being detected and/or highlighted to AI engine 80. In certain embodiments, the error detection can involve comparing the first test result to a javascript object notation ("JSON") template. An example of a template can be seen in FIG. 4, which will be discussed below. The JSON template can include a listing of all field objects and/or formatting characters that the test results are expected to include. In other words, the JSON template can be used to ensure that the test result is properly formatted and includes metadata files or information requested by the user.

If process 240 determines that the first test result does not match a header field or formatting character included in the template JSON, an error log that includes the detected errors of the first test result can be created, as shown in 250. The error log can include a record of the workflow, as well as any detected errors that have occurred. In some embodiments the error log can be formatted so that it can be inserted into the test result or included as an addendum to the test result. For example, in FIG. 2 the produced error log can be inserted into the test result, as shown in 260. In some embodiments, 260 can read through or parses error log 250, also referred to as an emulation server log, for information on the application programming interfaces ("APIs"), such as one or more completion or errors. While in some examples the error log is sent to AI engine 80, in other examples the error log is not sent to AI engine 80. In such other examples, the user can manually check the errors and adjust AI engine 80 accordingly. The error logs can be created in the same directory from which the JSON template is run. In those embodiments in which the error log is sent to AI engine 80, the error log can be saved in the memory of AI engine 80 or the first test result and the inserted error log can both be saved in the memory in AI engine 80.

In some non-limiting embodiments, after process 240 in FIG. 2 emulation server 220 can be turned off. The turning off of emulation server 220 can be either automatic or manual. Manually turning off emulation server 220 can include a user entering or providing an input that shuts down or turns off emulation server 220. In certain other non-limiting embodiments, emulation server 220 can be automatically or manually turned off after the second test result is produced and/or validated. For example, server emulator 220 can be automatically turned off when a successful status update is received from AI engine 80, while server emulator 220 can be manually turned off in response to a user input. A success post status, in certain embodiments, can be transmitted from AI engine 80 to server emulator 220 when a given scan does not reveal any errors.

When an error log with one or more detected errors is produced based on the first test result, AI engine 80 can respond by outputting or producing a second test result. In the second test result AI engine 80 can rely on the error log to fix any errors detected in the first test result. In certain embodiments the second test result can be validated using emulation server 220, while in other embodiments the second test result can simply be forwarded to server 10 or workstation 60 shown in FIG. 1. Workstation 60 can display the second test result using GUI 70.

Figure 3:
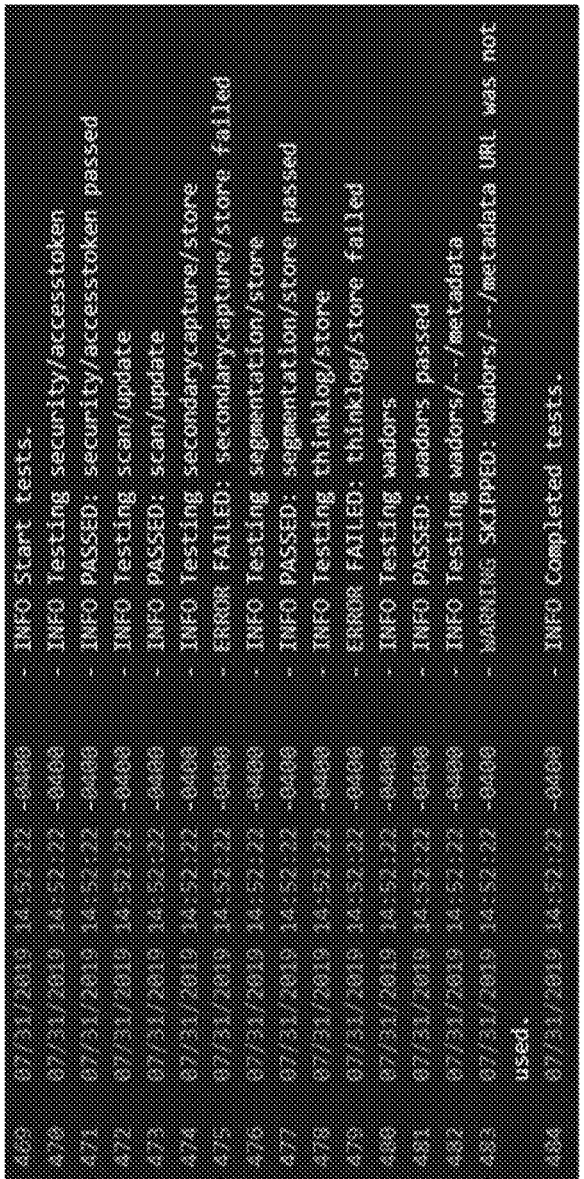
FIG. 3 illustrates a log according to certain embodiments of the disclosed subject matter.

FIG. 3 illustrates a log according to certain embodiments of the disclosed subject matter. In particular, FIG. 3 can illustrate a copy of an error log 300 that can be aggregated in step 250 of FIG. 2. Error log 300 can include a listing of the workflow involved in validating the requests, as shown in step 240 of FIG. 2. Each tested request can be labeled in error log 300 as PASSED, SKIPPED, or FAILED. A PASSED label 310 can be assigned when a coded value of the test result meets the JSON template. Assigning a PASSED label 310 can mean that the coded scenario has passed, and that the request to the URL included in the test result was made at least once. A SKIPPED label 340 can be assigned to a coded value of the test result that includes a URL request that was never made. In certain embodiments the SKIPPED label 340 can indicate when a workflow is configured to skip a particular API.

FAILED labels 320, 330 can be assigned when the coded value of the test result does not meet a header field or formatting character in the JSON template. In certain non-limiting embodiments, the error log can identify an API of server emulator 220 in which the error occurred. In other non-limiting embodiments, the error can illustrate a URL or token problem. For example, AI engine 80 may have failed to include the token in the test result, or included the wrong token in the test results. In another example, the error can be that AI engine 80 used an outdated version of an algorithm or an outdated version of the HTTP. For example, the outdated version of the algorithm can be sent back through some of the AI Engine scan results, and the scan results can be compared to those outputted by a different version of the algorithm. The comparison can be a string comparison, where one or more of the scan results are checked to determine that they are the same version. When an error is detected, therefore, the error log can make record of where the error has occurred and/or in which API the error has occurred.

In certain non-limiting embodiments, once AI engine 80 receives the error log, AI engine 80 can proceed to appropriately fix or correct the listed errors automatically. In other non-limiting embodiments, a user can be used to correct the output of AI engine 80 or the listed errors manually. The user, for example, can be a tester or programmer of AI engine 80. AI engine 80 can produce a second test result, which can fix the errors exhibited in the first test result. The first test result, for example, can be a preliminary result produced by AI engine 80 that can be internally outputted and reviewed by AI engine 80. The second test result, on the other hand, can be outputted to workstation 60. To provide proof that it has fixed the errors, the error log of the first test result can be inserted into the second test result. In some non-limiting embodiments, the second test result can independently be validated using a similar process, system, or method as shown in FIG. 2. In certain embodiments, the error log can be created even if no errors are detected. The error log can include information other than detected errors, such as HTTP request headers and/or bodies.

Figure 4:
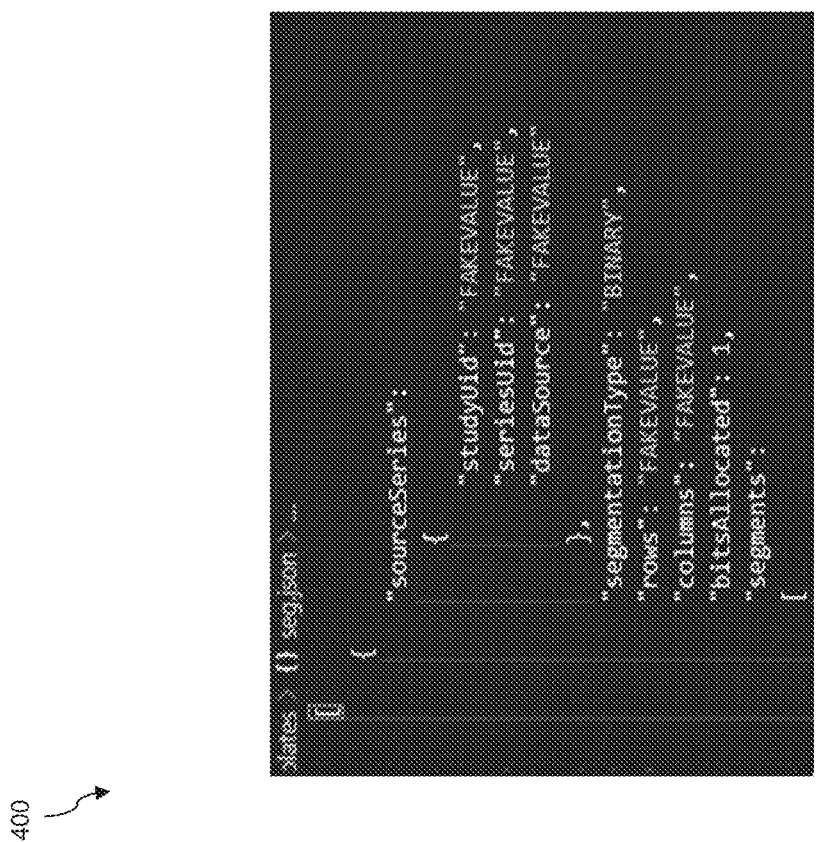
FIG. 4 illustrates a template according to certain embodiments of the disclosed subject matter.

FIG. 4 illustrates a template according to certain embodiments of the disclosed subject matter. In particular, FIG. 4 illustrates a JSON template 400 that can be used to detect errors in the test results produced by an AI engine, such as AI engine 80 shown in FIGS. 1 and 2. In certain embodiments the template can be customizable, allowing a user to add and/or remove different settings, values, or fields. Those settings or values removed will not be included as part of the error detection. As can be seen in FIG. 4, the template can include an identification of the instance, study, series, and/or data source of the image. The template can also include a segmentation type, a listing of the numbers of rows and columns, and a bit allocation amount. In some non-limiting embodiments, an error-free test result produced by an AI engine 80 can include each of the values included in FIG. 4. If any of the values are missing, an error can be detected and logged. The template can include both mandatory and optional values. While an error log can note that a test result failed to include an optional value, it can label it as PASSED 310 rather than FAILED 320, 330. In other words, mandatory values not included in the test result are detected as errors, while optional values not included can be detected but not marked as errors.

Figure 5:
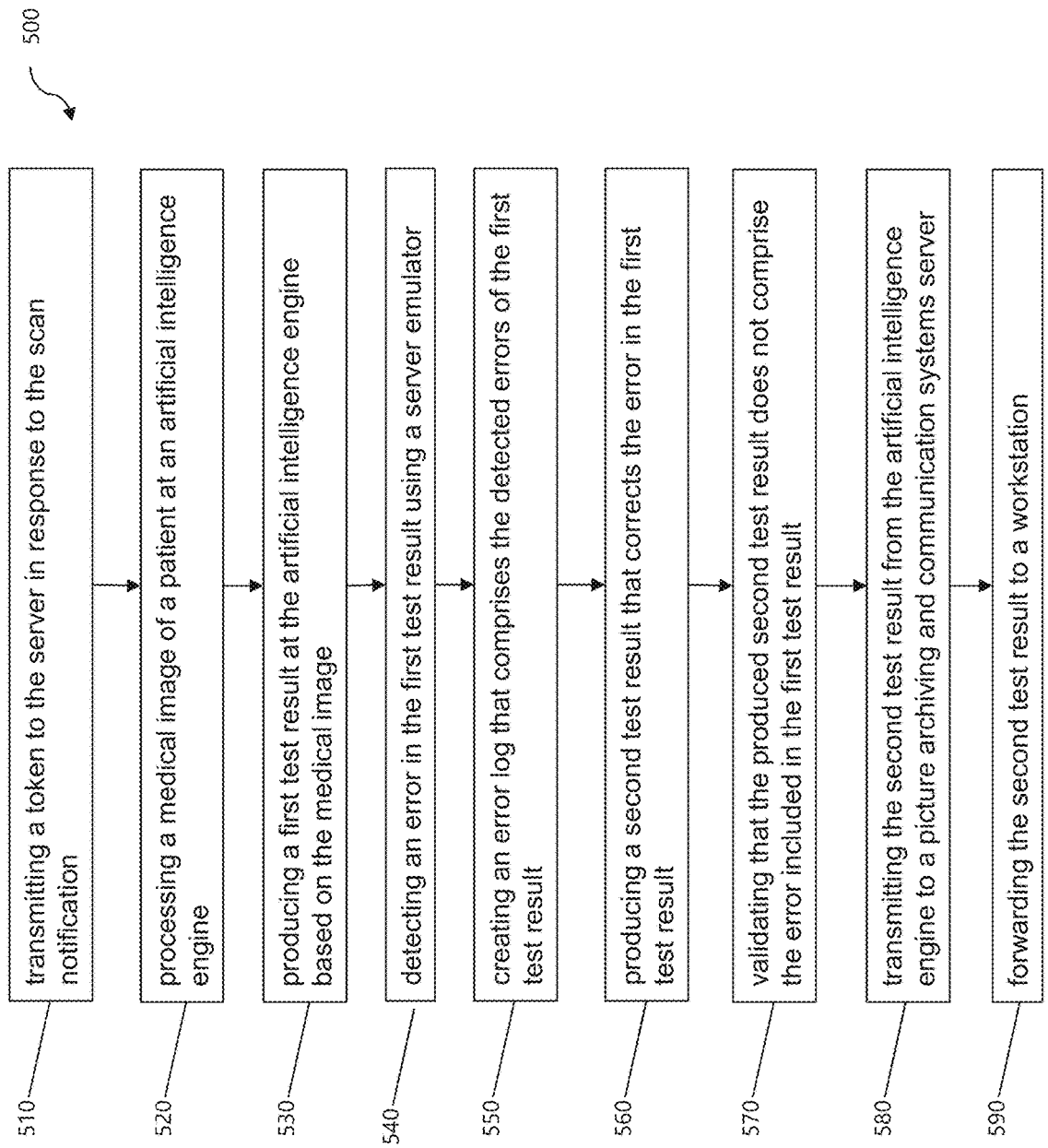
FIG. 5 illustrates a flow chart according to certain embodiments of the disclosed subject matter.

FIG. 5 illustrates a flow chart according to certain embodiments of the disclosed subject matter. In particular, an AI engine 80 can receive a scan notification, similar to the notification illustrated in FIG. 2. In response, AI engine 80 can transmit a token to an emulation server 220, as shown in step 510. The token can include, for example, a username and password for accessing the token. After transmitting the token, AI engine 80 can transmit a request, such as a GET request, for the medical image. Once accessed, AI engine 80 can process a medical image of a patient, as shown in step 520. The medical image, for example, can be a DICOM object. In step 530, AI engine 80 can produce a first test result based on the medical image. In certain embodiments the first test result can be an internal test result outputted within AI engine 80 or to server emulator 220. In other words, AI engine 80 can decide not to transmit the first test results to workstation 60.

Using a server emulator 220, AI engine 80 can detect an error in the first test, as shown in step 540. For example, the detection of the error can include comparing the first test results to a JSON template. In some embodiments, the comparison can help determine that the first test result does not match a header field or formatting character included in the JSON template. A header field or formatting character included in the first test result that does not match the JSON template can be logged as an error.

As shown in step 550, an error log can be created that includes the detected error of the first test result. The error log can also include any other information related to AI engine 80, including any transmitted request or received information. The error log, in certain embodiments, can be inserted into the second test result produced by AI engine 80. The error log can also identify the API of server emulator 220 in which the error occurred. In step 560, AI engine 80 can produce a second test result that corrects the error in the first test result. The second test result can be validated so that the result does not include the errors included in the first test result, as shown in step 570, or any other error. In addition, in certain embodiments the second test result can include an indication that the detected error was fixed.

As shown in step 580, the second test result can be transmitted from AI engine 80 to the PACS server, such as server 10 in FIG. 1. Alternatively, or in addition, AI engine 80 can directly transmit the second test result to a workstation, such as workstation 60 in FIG. 1, which can display the second test result to the user, as shown in step 590. Either the first test result and/or second test result can include a medical diagnosis made by the AI engine 80 based on the processed medical image. In some non-limiting embodiments, once the second test result is produced, server emulator 220 can be turned off.

In accordance with the disclosed subject matter, the method can repeat one or more steps of the method of FIG. 5, where appropriate. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates an example method for transferring and rendering a medical image record including the particular steps of the method of FIG. 5, this disclosure contemplates any suitable method for transferring and rendering a medical image record including any suitable steps, which can include all, some, or none of the steps of the method of FIG. 5, where appropriate. Furthermore, although this disclosure describes and illustrates particular components, devices, or systems carrying out particular steps of the method of FIG. 5, this disclosure contemplates any suitable combination of any suitable components, devices, or systems carrying out any suitable steps of the method of FIG. 5.

The embodiments disclosed above, help to improve the functioning of the PACS. In particular, using an emulator server can help to improve communication between AI engine 80 and PACS by helping to detect errors included in the test results produced by AI engine 80. Without such detection, erroneous test results can propagate throughout the PACS, leading PACS to exert additional resources identifying and removing such errors. Further, without the detection described above the erroneous test results can be forwarded to workstation 60, which can lead users to experience system errors. Detecting AI engine 80 errors using an emulator server can conserve network resources used by PACS and/or the workstation to identify and fix errors. The systems, methods, and apparatus described above, therefore, help to provide improvements to the functioning of server 10, AI engine 80, workstation 60, and other components of the PACS. This type of arrangement can also be particularly useful in embodiments in which the AI platform is provided by a third-party vendor, e.g., in a cloud-based deployment, in which a PACS developer does not have access to the detailed operation of AI engine 80, which can effectively be a "black box" to the PACS developer.

As described above in connection with certain embodiments, certain components, e.g., server 10 and workstation 60, can include a computer or computers, processor, such as processor 62 shown in FIG. 1, network, mobile device, cluster, or other hardware to perform various functions. Moreover, certain elements of the disclosed subject matter can be embodied in computer readable code which can be stored on computer readable media and which when executed can cause a processor 62 to perform certain functions described herein. In these embodiments, the computer and/or other hardware play a significant role in permitting the system and method for displaying medical image records. For example, the presence of the computers, processors, memory, storage, and networking hardware provides the ability to display medical image records in a more efficient manner. Moreover, the display of medical image records, cannot be accomplished with pen or paper, as such information is received over a network in electronic form.

The subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer program ("also known as a program, software, software application, script, or code") can be written in any form of programming language, including compiled or interpreted languages, declarative or procedural languages, and it can be deployed in any form, including as a stand-alone program or as a module, component, subroutine, object, or other unit suitable for use in a computing environment. A computer program can, but need not, correspond to a file in a file system. A program can be stored in a portion of a file that holds other programs or data ("e.g., one or more scripts stored in a markup language document"), in a single file dedicated to the program in question, or in multiple coordinated files ("e.g., files that store one or more modules, sub-programs, or portions of code"). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC. To the extent not expressly stated above, the disclosed subject matter is intended to encompass both sides of each transaction, including transmitting and receiving. One of ordinary skill in the art will readily understand that with regard to the features described above, if one component transmits, sends, or otherwise makes available to another component, the other component will receive or acquire, whether expressly stated or not.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

In the detailed description herein, references to "embodiment," "an embodiment," "one embodiment," "in various embodiments," "certain embodiments," "some embodiments," "other embodiments," "certain other embodiments," etc., indicate that the embodiment("s") described can include a particular feature, structure, or characteristic, but every embodiment might not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art("s") how to implement the disclosure in alternative embodiments.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method comprising:
processing a medical image of a patient at an artificial intelligence engine;
producing a first test result at the artificial intelligence engine based on the medical image;
detecting an error in the first test result using a server emulator;
producing a second test result that corrects the error in the first test result; and
transmitting the second test result from the artificial intelligence engine to a picture archiving and communication systems (PACS) server.

2. The method according to claim 1, wherein the first test result and the second test result comprises a medical diagnosis made by the artificial intelligence engine based on the medical image provided by the PACS server.

3. The method according to claim 1, wherein the error is corrected automatically by the artificial intelligence engine or manually by the user.

4. The method according to claim 1, wherein the detecting of the error further comprises:
comparing the first test result to a template javascript object notation; and
determining that the first test result does not match a header field or a formatting character included in the template javascript object notation.

5. The method according to claim 1, further comprising:
validating that the produced second test result does not comprise the error included in the first test result, and that the produced second test result does not comprise any other error.

6. The method according to claim 4, wherein the second test result comprises an indication that the detected error was fixed.

7. The method according to claim 1, further comprising:
creating an error log that comprises the detected error of the first test result; and
inserting the error log into the transmitted second test results.

8. The method according to claim 6, wherein the error log identifies an application programming interface of the server emulator in which the error occurred.

9. The method according to claim 1, further comprising:
receiving a scan notification at the artificial intelligence engine; and
transmitting a token to the server emulator in response to the scan notification.

10. The method according to claim 8, wherein the token can include a username and password.

11. The method according to claim 1, wherein the medical image is a digital imaging and communications in medicine ("DICOM") object.

12. The method according to claim 1, further comprising:
forwarding the second test result to a workstation, wherein the workstation displays the second test result to a user.

13. The method according to claim 1, further comprising:
turning off the server emulator after the second test result is produced.

14. An artificial intelligence engine comprising:
at least one memory comprising computer program code; and
at least one processor;
wherein the computer program code is configured, when executed by the at least one processor, to cause the artificial engine to:
process a medical image of a patient;
produce a first test result based on the medical image;
detect an error in the first test result using a server emulator;
produce a second test result that corrects the error in the first test result; and
transmit the second test result to a picture archiving and communication systems (PACS) server.

15. The artificial intelligence engine according to claim 13, wherein the first test result and the second test result comprises a medical diagnosis based on the medical image provided by the PACS server.

16. The artificial intelligence engine according to claim 13, wherein the computer program code is configured, when executed by the at least one processor, to cause the artificial engine to:
compare the first test result to a template javascript object notation; and
determine that the first test result does not match a header field or a formatting character included in the template javascript object notation.

17. The artificial intelligence engine according to claim 13, wherein the computer program code is configured, when executed by the at least one processor, to cause the artificial engine to:

validate that the produced second test result does not comprise the error included in the first test result, and that the produced second test result does not comprise any other error.

18. The artificial intelligence engine according to claim 13, wherein the computer program code is configured, when executed by the at least one processor, to cause the artificial engine to:

create an error log that comprises the detected error of the first test result; and insert the error log into the transmitted second test results.

19. The artificial intelligence engine according to claim 13, wherein the computer program code is configured, when executed by the at least one processor, to cause the artificial engine to:

receive a scan notification at the artificial intelligence engine; and transmit a token to the server in response to the scan notification.

20. The artificial intelligence engine according to claim 13, wherein the computer program code is configured, when executed by the at least one processor, to cause the artificial engine to:

forward the second test result to a workstation, wherein the workstation displays the second test result to a user.

* * * * *